United States Patent [19]
Maki et al.

[11] Patent Number: 4,732,891
[45] Date of Patent: Mar. 22, 1988

[54] PLACENTA-DERIVED ANTICOAGULATING SUBSTANCE, PROCESS FOR PREPARING SAME AND ANTICOAGULANT COMPRISING SAME AS AN EFFECTIVE COMPONENT

[75] Inventors: Masahiro Maki, Akita; Hideo Tani, Kodaira, both of Japan

[73] Assignee: Kowa Co., Ltd., Nagoya, Japan

[21] Appl. No.: 909,296

[22] Filed: Sep. 19, 1986

[30] Foreign Application Priority Data

Sep. 30, 1985 [JP] Japan ................................ 60-217512

[51] Int. Cl.$^4$ ..................... C07K 15/06; A61K 35/50; A61K 37/24
[52] U.S. Cl. ....................................... 514/21; 424/85; 424/88; 530/350; 530/416; 530/420; 530/842; 530/851; 530/399
[58] Field of Search .................... 424/85, 88; 530/416, 530/420, 842, 851, 350, 399; 514/21

[56] References Cited

U.S. PATENT DOCUMENTS

| | | | |
|---|---|---|---|
| 3,310,471 | 3/1967 | Parcells | 530/399 X |
| 3,409,605 | 11/1968 | Florini | 530/399 |
| 4,217,339 | 8/1980 | Bohn | 530/416 X |
| 4,219,467 | 8/1980 | Pende et al. | 530/399 |
| 4,254,021 | 3/1981 | Bohn et al. | 530/851 X |
| 4,301,064 | 11/1981 | Bohn | 530/851 X |
| 4,348,316 | 9/1982 | Bohn | 530/851 X |
| 4,500,451 | 2/1985 | Bohn et al. | 530/851 X |
| 4,507,229 | 3/1985 | Bohn | 530/842 X |
| 4,529,594 | 7/1985 | Hayashi et al. | 530/413 X |
| 4,592,863 | 6/1986 | Bohn et al. | 530/350 |
| 4,599,318 | 7/1986 | Bohn et al. | 530/413 X |

OTHER PUBLICATIONS

Eur. J. Biochem. 151, 625–629 (1985), Reutelingsperger et al.

Primary Examiner—Howard E. Schain
Attorney, Agent, or Firm—& Maier Oblon, Fisher, Spivak, McClelland

[57] ABSTRACT

Novel human placenta-derived anticoagulating substances having the following properties:
(1) molecular weight of 34,000±2,000 determined by SDA-polyacrylamide gel electrphoresis under reduced state;
(2) isoelectric point of 4.7±0.1 determined by isoelectric column electrophoresis using an ampholite;
(3) stability
 inactivated by heat treatment at 50° C. to 30 minutes, stable at a pH of 4–10, and stable in plasma at 37° C. for 30 minutes;
(4) activity
 capable of prolonging a recalcification time, a prothrombin time, and an activated partial thromboplastin time; and
(5) the existence of several amino acids including aspartic acid, threonine, serine, and so on; are prepared by homogenizing human placenta, subjecting the resulting homogenate to centrifugal separation, extracting an anticoagulating substance from the residue or from a microsome fraction contained in the supernatant with a surface active agent and/or a chelating agent, and purifying and isolating the substance from the extract.

The anticoagulating substances have a high anticoagulating activity and exhibit a higher activity in the state where the tissue thromboplastin activity is exacerbated or in the state of exacerbating the coagulation. Hence, the anticoagulant containing the substance as an effective component has reduced side effects and is thus harmless.

10 Claims, 3 Drawing Figures

PLACENTA-DERIVED ANTICOAGULATING SUBSTANCE, PROCESS FOR PREPARING SAME AND ANTICOAGULANT COMPRISING SAME AS AN EFFECTIVE COMPONENT

BACKGROUND OF THE INVENTION

1. Field of the Invention

This invention relates to a novel anticoagulating substance, a process for preparing the substance, an anticoagulant comprising the substance as an effective component, and a medical composition.

2. Description of the Prior Art

The coagulation of blood is considered to start from the development of thromboplastin activity, followed by activation of factor X and V in the blood, further activation of prothrombin into thrombin and final conversion of fibrinogen into fibrin by the action of the thrombin.

For the treatment of diseases ascribed to the coagulation, it is effective to use a substance which is able to impede or deactivate various coagulation factors which take part in the coagulation mechanism, i.e. an anticoagulating substance. Currently known anticoagulating substances include heparin, heparin cofactor-II, antithrombin-III, $\alpha_2$-macroglobulin, $\alpha_1$-trypsin inhibitor, $C_1$-esterase inhibitor, protein C and the like.

In recent years, Chris P.M. Reutelingsperger et al found out, as reported in Eur. J. Biochem., 151, 625–629 (1985), a novel substance having the anticoagulating activity and a molecular weight of 32 kDa from arteries of the human umbilical cord.

However, most known anticoagulating substances have been merely confirmed to exist and it is only heparin that is now in use as a medicine. However, since heparin has the side effect of a tendency toward bleeding, the manner and amount of use are very strictly limited. Thus, it is not satisfactory as the anticoagulating agent from the standpoint of safety.

The substance found by Reutelingsperger et al is completely different from the substance of the invention for the reason described hereinafter. In addition, the activity of the substance has been determined only in the form of a mixture and thus, such a substance is not considered to be useful for practical service.

Accordingly, there is a demand of development of better anticoagulants.

SUMMARY OF THE INVENTION

The present inventors made intensive studies on anticoagulants which are free of side effects and harmless to the living body. As a result, it has been found that a novel anticoagulating substance is obtained from placentae, particularly human placentae, which contain a large amount of tissue thromboplastin along with the factor XIII and the fibrinolytic inhibition factor, which is considered to have a tendency toward thrombotic formation and which has a specific state from the standpoint of the coagulating mechanism. The novel anticoagulation substance which is described above is isolated from a homogenate of human placentae, especially from residue and microsome fraction in the supernatant obtained by centrifugal separation of the homogenate of human placentae. The present invention is accomplished based on the above finding.

The present invention provides a human placenta-derived, novel anticoagulating substance having the following properties, a process for preparing the same and an anticoagulant having the substance as its effective component.

(1) Molecular weight (SDS-polyacrylamide gel electrophoresis, reduced state) 34,000±2,000;

(2) isoelectric point (isoelectric column electrophoresis using an ampholite) 4.7 ±0.1;

(3) stability
  (a) inactivated by heat treatment at 50° C. for 30 minutes,
  (b) stable at a pH of 4–10,
  (c) stable in plasma at 37° C. for 30 minutes;

(4) activity
  (a) capable of prolonging a recalcification time,
  (b) capable of prolonging a prothrombin time,
  (c) capable of prolonging an activated partial thromboplastin time; and (5) analysis of amino acids
  the existence of aspartic acid, threonine, serine, glutamic acid, proline, glycine, alanine, ½ cystine, valine, methionine, isoleucine, leucine, tyrosine, phenylalanine, histidine, lysine and arginine is recognized by the analysis of amino acids.

DETAILED DESCRIPTION OF THE INVENTION AND PREFERRED EMBODIMENTS

Figure 1:
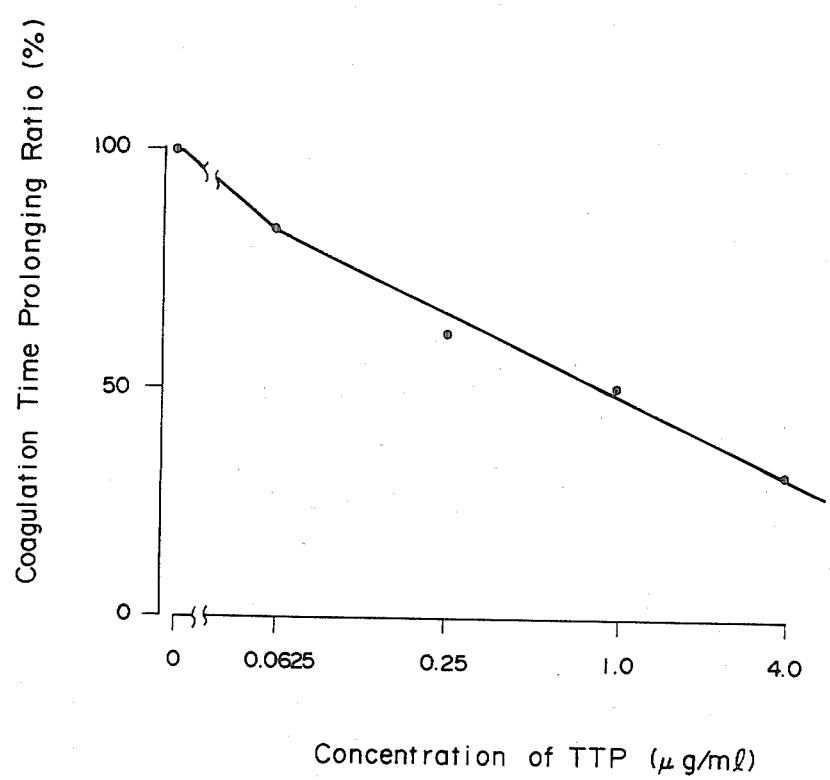
FIG. 1 is a graphical representation of the relation between concentration of TTP added to the fresh blood of rabbit and coagulation time-prolonging ratio.

The anticoagulating substance of the invention (which may be hereinafter referred to as "present substance") can be prepared, for example, as follows.

A placenta homogenate is first prepared from the human placenta and centrifugally separated. The homogenating operation is effected as follows: the amnion is removed from the placenta and sufficiently washed with a physiological saline solution, followed by homogenization by the use of the Waring blender and Polytron. The resulting homogenate is subjected to centrifugal separation to obtain a supernatant and a sediment or residue.

The supernatant is further fractionated by ultracentrifugal separation at 50,000 to 100,000 x g to get a microsome fraction. The residue separated from homogenate and the thus obtained microsome fraction are washed enough with a buffer solution, and are collected respectively by centrifugal or ultracentrifugal separation as washed residue and microsome. Both washed materials are combined together and immersed in a solution of chelating agent and/or surface active agent. The chelating agents include such as EDTA, EGTA, citrate, oxalate, nitrilotriacetic acid chelate, phosphoric acid and the like, and the surface active agents include such as Triton ® X - 100, Lubrol ®, SDS, deoxycholic acid and the like. The thus obtained material treated by the chelating agent and/or surface active agent is allowed to stand overnight at 4° to 8° C. A supernatant was collected and subjected to centrifugal separation to obtain extract. Above mentioned extracting procedure may be preferably effected in the presence of both a chelating agent and a surface active agent. The thus obtained extract is further subjected to ammonium sulfate fractionation. The ammonium sulfate fractionation is effected by two step procedure. First, solid ammonium sulfate is added to the extract until 35% saturation concentration, and a supernatant is subjected to centrifugal separation. Then, solid ammonium sulfate is added to the supernatant until reaching 85% saturation concentration and obtained ammonium sulfate fraction as a precipitate by centrifugal separation. The resulting ammonium sulfate fraction is purified by known isolation and purification procedures including, for example, dialysis, ion exchange chromatography, gel filtration, adsorption chromatography, hydrophobic chromatography, isoelectric point column electrophoresis, affinity chromatography using lectin or an antibody and the like, thereby obtaining the present substance. These procedures may be used singly or in combination. For example, a fraction obtained by subjecting the extract with a chelating agent and/or a surface active agent to ammonium sulfate fractionation is sufficiently dialyzed. The resulting dialyzate is subjected to elution according to a linear concentration gradient method using DEAE-Toyopearl and the resultant active fraction is dialyzed, followed by passage through Blue Sepharose. Subsequently, the active fraction is concentrated and subjected to gel filtration using Sephadex G-100 to obtain the present substance.

The thus obtained present substance has such properties as indicated before and the measurements and results for these properties are more particularly described.

(1) Measurement of molecular weight

The molecular weight measured by SDS-polyacrylamide gel electrophoresis (12% polyacrylamide gel; reduced state) was found to be 34,000 ±2,000. The measurement by gel filtration using Sephadex G-100 revealed elution at the same position as low molecular weight urokinase (molecular weight about 34,000).

(2) Measurement of isoelectric point

According to the measurement by an isoelectric point column electrophoresis using ampholite (pH 3.5–10) at 300 V for 48 hours, the isoelectric point was found to be 4.7±0.1 (4° C.). Moreover, an isoelectric point electrophoresis using a polyacrylamide gel and ampholite (pH 4.0–6.0) in which the sample was subjected to electrophoresis at 10 W for 2 hours revealed an isoelectric point of 4.9 (10° C.).

(3) Stability tests (a) Stability against heat treatment

The present substance was thermally treated at different temperatures (0°–90° C.) for 30 minutes and the anticoagulating activity was measured according to the recalcification time method. As a result, it was found that the activity completely disappeared at temperatures not lower than 50° C.

(b) pH stability

Buffer solutions having different pH values of 2.5 to 10.0 were added, followed by treatment at 4° C. for 18 hours and at 25° C. for 3 hours. Thereafter, the remaining anticoagulating activity was measured by the recalcification method. As a result, the activity did not lower in the pH range of 4 to 10.

(c) Stability in plasma

The present substance was added to plasma and incubated at 37° C. for 30 minutes, followed by measurement of a remaining anticoagulating activity by the recalcification time method. No lowering of the activity was found.

(4) Activity (a) Activity on recalcification time

One hundred microliters of standard plasma (Ortho Diagnostic Systems Inc.) and 100 microliters of a solution of the present substance were mixed. Three minutes after the addition, 100 microliters of a 0.025 M calcium chloride solution was added to the mixture and subjected to measurement of the coagulation time. As a result, a strong action of prolonging recalcification time was recognized as shown in Table 1.

TABLE 1

| Amount of the present substance (μg) | 0 | 0.075 | 0.75 |
|---|---|---|---|
| Coagulation time (seconds) | 263 | 506 | 1509 |

(b) Action on prothrombin time (PT)

One hundred microliters of PT reagents (Simplastin: Warner Lambert Co., Ltd.) and 100 microliters of a solution of the present substance were mixed. After 3 minutes, 100 microliters of standard plasma were added, followed by measurement of the coagulation time. The results are shown in Table 2, revealing a strong PT-prolonging action.

TABLE 2

| Amount of tissue thromboplastin (μg) | 1 | 1 | 1 | 10 | 10 | 10 |
|---|---|---|---|---|---|---|
| Amount of the present substance (μg) | 0 | 0.1 | 0.3 | 0 | 0.1 | 0.3 |
| Coagulation time (seconds) | 202 | 275 | 956 | 88 | 111 | 239 |

(c) Action on activated partial thromboplastin time (APTT)

Ten microliters of APTT reagent (activated thrombophax, Ortho Diagnostic Systems Inc.) and 90 microliters of a solution of the present substance were mixed. After 2 minutes, 100 microliters of standard plasma was added to the mixture. After 6 minutes, 100 microliters of a 0.025 M calcium chloride solution was added in order to determine the coagulation time. As a result, a strong APTT prolonging action was recognized as shown in Table 3.

TABLE 3

| APTT reagent (μl) | 10 | 10 | 10 |
|---|---|---|---|
| Amount of the present substance (μg) | 0 | 2 | 5 |
| Coagulation time (seconds) | 101 | 113 | 276 |

(5) Amino acid composition

The present substance was hydrolyzed with 6N hydrochloric acid at 110° C. for 24 hours and subjected to an amino acid analyzing system of the Waters high performance liquid chromatography (Waters HPLC). The results are shown in Table 4.

TABLE 4

| Composition of Amino Acid | mol % |
|---|---|
| Aspartic acid | 9.8 |
| Threonine | 7.0 |
| Serine | 6.3 |
| Glutamic acid | 13.3 |
| Proline | 2.0 |
| Glycine | 7.5 |
| Alanine | 8.0 |
| ½ Cystine | 0.3 |
| Valine | 4.6 |
| Methionine | 1.8 |
| Isoleucine | 5.3 |
| Leucine | 11.8 |
| Tyrosine | 3.6 |
| Phenylalanine | 4.2 |
| Histidine | 1.4 |
| Lysine | 7.2 |
| Arginine | 6.2 |

According to Reutelingsperger et al, the molocular weight of their substance was measured by SDS-PAGE, and it was only confirmed that the substance was a protein inactivated by thermal treatment at 56° C. without being isolated or identified. However, in view that this substance was obtained by extraction of the umbilical cord with a tris-HCl buffer, the present substance is considered to differ from the substance obtained by Reutelingsperger et al.

When the present substance is used as an effective component of an anticoagulant, the preparation may be an injection. The injection is preferably in the form where a freeze-dried powder is dissolved in distilled water or physiological saline solution for injection and administered. The injection site may conveniently be intravenous.

The amount of administration is preferably in the range of from 10 μg to 10 mg/kg.day. It should be noted that the present substance presents no abnormality on use within the above range of the amount of administration and is thus harmless. For the preparation of the present substance as an injection, albumin, gelatin or mannitol may be added as a stabilizer. The addition of these stabilizers can prevent decomposition and adsorption during the preparation process and can improve the storage stability of the preparation.

The present substance has a high anticoagulating activity and exhibits a higher activity in the state where the tissue thromboplastin activity is exacerbated or in the state of exacerbating the coagulation. Hence, the anticoagulant containing the substance as an effective component has reduced side effects and is thus harmless.

The present invention is described by way of examples.

EXAMPLE 1

(i) Five human placentae (about 2,500 g) were subjected to removal of the membranes therefrom and sufficiently washed with physiological saline solution. Thereafter, 2 liters of a 50 mM tris-hydrochloric acid buffer solution was added to the pieces of placenta and homogenized by Waring blender and further by Polytron. The resulting homogenate was subjected to centrifugal separation at 7,000 r.p.m. for 15 minutes to obtain sediment. The thus obtained sediment was washed by adding 2 liters of the same buffer solution, homogenized with Polytron and subjected to centrifugal separation at 7,000 r.p.m. for 15 minutes. The above procedure was repeated several times till the blood component was removed to finally obtain a 930 g of washed sediment.

(ii) About 2 liters of a 50 mM trishydrochloric acid buffer solution containing 50 mM of EDTA was added to 900 g of the sediment obtained in (i), followed by homogenization by the use of the Waring blender. The resulting homogenate was agitated at 4° C. overnight, followed by centrifugal separation at 7,000 r.p.m. for 15 minutes to obtain 2 liters of an extract.

(iii) Solid ammonium sulfate was added to the extract obtained in (ii) to a saturation of 35% and allowed to stand at 4° C. for 30 minutes to several hours, followed by centrifugal separation at 7,000 r.p.m. for 15 minutes to collect a supernatant. Ammonium sulfate was further added to the supernatant to a saturation of 85% and allowed to stand at 4° C. for 2 hours, followed by centrifugal separation at 7,000 r.p.m. for 15 minutes to collect sediment. The thus obtained sediment was dissolved in a small amount of a 20 mM tris-hydrochloric acid buffer solution and sufficiently dialyzed against the same buffer solution at 4° C. overnight. The precipitate formed during the dialysis was removed by centrifugal separation at 7,000 r.p.m. for 15 minutes to obtain 390 ml of a dialyzate.

(iv) The dialyzate was adsorbed on DEAET-oyopearl ($\phi$5.5×19 cm) equilibrated with a 20 mM tris-hydrochloric acid buffer solution (pH 7.4) and sufficiently washed with the buffer solution. Thereafter, 4 liters of the same buffer solutions containing from 0 to 0.3M sodium chloride were used to cause 20 ml of each fraction to be eluted according to the linear concentration gradient method. The active fraction was found to be eluted in the vicinity of a sodium chloride concentration of approximately 0.15M and 380 ml of the active fraction was obtained.

(v) The thus obtained active fraction was sufficiently dialyzed against a 0.1M phosphate buffer solution (pH 7.0) at 4° C. overnight and passed through a Blue Sepharose column ($\phi$2.5×12 cm) equilibrated with the same buffer solution as used above. The passed fraction (480 ml) exhibiting an absorption at $A_{280}$ was collected and concentrated by the use of a DIAFLO membrane filter YM-10.

(vi) The concentrate obtained in (v) was subjected to gel filtration using Sephadex G-100 and eluted with physiological saline solution to make 8 ml of each fraction. The active fractions 88 to 104 were collected and concentrated by ultrafiltration to obtain 14.5 ml of the present substance solution (weight of proteins 136.1 mg, Lowry method).

The yields of the proteins obtained in the respective purification steps are shown below.

| Step | Weight of proteins (mg) |
|---|---|
| step (ii) (EDTA extraction) | 7226 |
| step (iii) (ammonium sulfate fractionation, dialysis) | 3184 |
| step (iv) (adsorption on DEAE-Toyopearl) | 531 |
| step (v) (passage through Blue Sepharose) | 163 |
| step (vi) (gel filtration on Sephadex G-100) | 136 |

EXAMPLE 2

One gram of the washed sediment obtained in (i) of Example 1 was mixed with 1 ml of each of 50 mM tris-hydrochloric acid buffer solutions (pH 7.4) containing different concentrations of EDTA (0–200 mM) and homogenized, followed by allowing to stand at 4° C. overnight and centrifugal separation at 7,000 r.p.m. for 15 minutes to obtain 1 ml of a supernatant. The supernatant was subsequently subjected to SDS-polyacrylamide gel electrophoresis and western plotting and then to immunological staining with rabbit antiserum, followed by quantitative determination of the present substance by means of a densitometer. The results are shown in Table 5 below.

TABLE 5

| Concentration of EDTA (mM) | 200 | 100 | 50 | 25 | 12.5 | 0 |
|---|---|---|---|---|---|---|
| Content of the present substance (μg/g of washed sediment) | 252 | 250 | 268 | 288 | 51 | 6 |

From the above results, it will be seen that the present substance can be efficiently extracted using an equivalent tris-hydrochloric buffer solution containing not less than 12.5 mM, preferably from 20 to 100 mM, of EDTA.

EXAMPLE 3

Three human placentae (about 1,500 g) were used to obtain 510 g of a washed sediment in the same manner as in (i) of Example 1.

To 10 g of the above obtained washed sediment, 10 ml of a 50 mM tris-hydrochloric acid buffer solution (pH 7.4) containing 50 and 100 mM of chelating agents shown below was added, followed by homogenization. The resulting homogenate was allowed to stand at 4° C. overnight, followed by centrifugal separation at 7,000 r.p.m. for 15 minutes to collect 10 ml of a supernatant.

The thus obtained supernatant was subjected to SDS-polyacrylamide gel electrophoresis, followed by dyeing proteins to detect a protein band at the same mobility position as detected for the inventive substance.

The samples which revealed the protein band were further subjected to the steps (iii), (iv), (v) and (vi) of Example 1, i.e. fractionation by ammonium sulfate, ion exchange by DEAE-Toyopearl ($\phi 1.4 \times 7$ cm), passage through on Blue Sepharose ($\phi 1.4 \times 6.5$ cm) and gel filtration by Sephadex G-100 ($\phi 2.0 \times 90$ cm) in this order to obtain a purified inventive substance.

The final yields (mg, determined by Lowry Method) of the purified samples are shown in Table 6.

In the table, "—" and "ND" mean that no corresponding protein band was detected in SDS polyacrylamide gel electrophoresis and not done, respectively.

TABLE 6

| Chelating agent | Yield (mg) Concentration | |
|---|---|---|
|  | 50 mM | 100 mM |
| EDTA | 1.69 | 1.89 |
| GEDTA* | 0.74 | 1.37 |
| Oxalic acid | 1.97 | ND |
| Citric acid | — | 1.24 |
| Sodium nitrilotriacetic acid | 0.60 | 1.39 |
| Phosphoric acid | ND | 0.76 |

*Glycoletherdiamine-N,N,N',N',—tetraacetic acid

From the above results, it will be seen that the present substance can be efficiently extracted or purified by using a chelating agent having a strong chelating effect to calcium and a tris-hydrochloric acid buffer solution of at least equimolar to a washed sediment.

EXAMPLE 4

To 1 g of a washed sediment obtained in the same manner as in Example 3, 4 ml of a 50 mM trishydrochloric acid buffer solution (pH 7.4) containing 0.5 or 1.0% of each of surface active agents shown below was added. The mixed solution was allowed to stand overnight and then subjected to centrifugal separation to collect supernatant. The resulting supernatant was subjected to SDS-polyacrylamide gel electrophoresis to detect an extraction of the inventive substance. The results are shown in Table 7.

Those samples which a dyed protein band was detected at a mobility position corresponding to the inventive substance are indicated by "+", and those which a dyed protein band was not clearly detected are indicated by "±" in the Table.

TABLE 7

| Surface active agent | Detection of dyed band Concentration | |
|---|---|---|
|  | 0.5% | 1.0% |
| Triton X-100 ® (Nonionic surface active agent) | ± | + |
| Lubrol ® (Nonionic surface active agent) | + | + |
| SDS | + | + |
| Deoxycholic acid | ± | + |

Then, the present substance is purified from Lubrol extraction by the following way. 40 ml of a 50 mM tris-hydrochloric acid buffer solution (pH 7.4) containing 1% of Lubrol was added to 10 g of a washed sediment and homogenized. The resulting homogenate was allowed to stand at 4° C. overnight and centrifugally separated at 7,000 r.p.m. for 15 minutes to collect a supernatant. 40 ml of the supernatant was subjected to a gel filtration using Sephadex G-100 ($\phi 4.8 \times 75$ cm), followed by ion exchange by DEAE-Toyopearl ($\phi 1.4 \times 7$ cm). Thereafter, the above sample was subjected to a gel filtration using Sephadex G-100 ($\phi 2.0 \times 90$ cm) again to obtain 0.95 mg (determined by Lowry Method) of the purified inventive substance.

The above results show that the present invention can be extracted efficiently by using a surface active agent and a tris-hydrochloric acid buffer solution of at least equimolar to a washed sediment

EXAMPLE 5

The extract prepared in the same manner as in (i) and (ii) of Example 1 was mixed with ammonium sulfate solutions having different saturations of 40 to 80% and allowed to stand at 4° C. for 30 minutes or over, followed by centrifugal separation at 7,000 r.p.m. for 15 minutes to separate a supernatant and a precipitate from each other.

The supernatant and the precipitate were, respectively, dialyzed against a 50 mM tris-hydrochloric acid buffer solution (pH 7.4) at 4° C. overnight, followed by concentration and quantitative determination of the present substance in the same manner as in Example 2. The results are shown in Table 8.

TABLE 8

| Saturation of Ammonium sulfate (%) | 40 | | 60 | | 80 | |
|---|---|---|---|---|---|---|
| Fraction | supernatant | precipitate | supernatant | precipitate | supernatant | precipitate |
| Content of | 261 | 8 | 47 | 248 | 23 | 313 |

TABLE 8-continued the present
substance
(μg/g of
washed sediment)

As will be seen from the above results, the present substance can be isolated by treating the chelating agent extract with an ammonium sulfate solution having a saturation not higher than 40% to remove impurities therefrom and concentrating the treated extract by the use of an ammonium sulfate solution having a saturation of not less than 80%.

EXAMPLE 6

(i) Four human placentae (1950 g) were sufficiently washed with physiological saline solution, removed the membranes and blood vessels and minced. Two liters of a 50 mM tris-hydrochloric acid buffer solution (pH 7.4) was added, followed by breakage into pieces by means of Polytron and ground by a Teflon homogenizer. The resulting homogenate was centrifugally separated at 7,000 r.p.m. for 15 minutes to collect a supernatant.

(ii) The supernatant was subjected to ultracentrifugation at 55,000 g for 1 hour to obtain a microsome fraction in the sediment. This microsome fraction was suspended in 50 ml of a 20 mM tris-hydrochloric acid buffer solution (pH 7.4) and mixed with 10 ml of 10% Triton X-100, followed by ultrasonic treatment. Thereafter, 500 ml of a refrigerated mixed solvent of ethanol and ether at a mixing ratio of 3:2 was added and shaked in a low temperature chamber (4° C.) for 2 hours. The shaked solution was centrifugally separated at 2,000 r.p.m. for 10 minutes and the resulting sediment was suspended in 500 ml of cold ether and shaked, followed by centrifugal separation at 2,000 r.p.m. for 10 minutes to collect a sediment. The sediment was suspended in about 50 ml of a 20 mM tris-hydrochloric acid buffer solution (pH 7.4) and, after supersonic treatment, subjected to ultracentrifugation at 105,000 g for 1 hour to obtain 53 ml of a supernatant (microsome-soluble fraction).

(iii) The solution obtained in (ii) was subjected to concanavalin A Sepharose column ($\phi 1.4 \times 5.5$ cm) to collect 63 ml of a fraction exhibiting an absorption of $OD_{280}$ from a non-adsorbed fraction. The fraction was adsorbed on a DEAE-Sephadex column ($\phi 1.4 \times 8.5$ cm) and washed sufficiently with a 20 mM tris-hydrochloric acid buffer solution (pH 7.4). Subsequently, 150 ml of the same buffer solution as used above but containing 0–0.5M sodium chloride was used to cause each 3 ml of fractions to be eluted according to a linear concentration gradient method. 64 ml of the active fractions were concentrated and subjected to gel filtration ($\phi 2.5 \times 8.6$ cm) using Sephacryl S-200, followed by eluation with physiological saline solution in such a way as to make 3 ml of each fraction. As a result, 33.5 ml of 85 to 95 fractions exhibiting the activity were obtained. The activity was measured according to recalcification time method.

(iv) The fractions were further subjected to gel filtration ($\phi 2.0 \times 90$ cm) using Sephadex G-100 and eluated with physiological saline solution to make 2 ml of each fraction to obtain active fraction Nos. 74–89. The fractions were concentrated by ultrafiltration to obtain 3.0 ml of a purified preparation of the present substance (protein content 3.8 mg (Lowry method)). The thus obtained present substance which exhibited a single band by SDS.polyacrylamide gel electrophoresis is thus considered to be a single component.

EXAMPLE 7

(i) Forty five human placentae (about 20 kg) were sufficiently washed with physiological saline solution, removed the membranes therefrom and minced. To the minced placentae was added about 16 liters of a tris-HCl buffer solution (pH 7.4), followed by reduction into pieces by the Waring blender and then by Polytron. The resulting homogenate was centrifugally separated at 7,000 r.p.m. for 15 minutes to collect a supernatant. The sediment obtained by the centrifugal separation was again mixed with about 13 liters of a 50 mM tris-HCl buffer solution (pH 7.4) and minced and subjected to centrifugal separation to obtain a supernatant.

(ii) The supernatants obtained by the two mincing and centrifugal separation operations were combined (about 30 liters) and further centrifugally separated at 45,000 r.p.m. by menas of a sharpless ultra-high speed centrifugal separator to obtain a microsome fraction as sediment. Thereafter, 3 liters of a 50 mM tris-HCl buffer solution (pH 7.4) was added to the microsome and ground by means of a Teflon homogenizer, followed by collection of sediment by means of the sharpless ultra-high speed centrifugal separator to obtain washed microsome.

(iii) About 4 liters of a 50 mM tris-HCl buffer solution (pH 7.4) containing 20 mM EDTA was added to the thus obtained microsome and ground, followed by agitation by the use of a magnetic stirrer overnight. Thereafter, the mixture was again subjected to centrifugal separation by the sharpless ultra-high speed centrifugal separator to obtain EDTA extract from the microsome as supernatant.

(iv) The EDTA extract from the microsome was dialyzed to remove the EDTA, followed by purification by ion exchange chromatography, passage through Blue Sepharose and gel filtration in the same manner as in Example 1. As a consequence, 95 mg of an anticoagulating substance was obtained from the microsome of about 20 kg of the placentae.

EXAMPLE 8

The present substance obtained in Example 1 was subjected to measurement of an anticoagulating action by a thromboelastograph.

(1) Experiment of addition to fresh blood:
(Measuring method)

Ten microliters of physiological saline solution of the present substance (final concentrations, 0, 0.15, 0.5, 1.5, 5, 15 μg/ml) was added to 490 microliters of fresh blood and sufficiently mixed, after which the mixture was set in a thromboelastograph to make a thromboelastogram over 70 minutes. The total time of r and R values was determined as a coagulation time.

The bloods used were those of rabbit and men. The results are indicated by ratios to a control value which is obtained without addition of the present substance and shown in Table 9.

TABLE 9

| | Coagulation Time-prolonging Ratio (%) | | | | | |
|---|---|---|---|---|---|---|
| | Amount of the Present Substance (μg/ml) | | | | | |
| Blood | 0 | 0.15 | 0.5 | 1.5 | 5 | 15 |
| Rabbit (n = 4) | 100 | 98 | 116 | 122 | 191 | 204 |

TABLE 9-continued

| | Coagulation Time-prolonging Ratio (%) | | | | | |
|---|---|---|---|---|---|---|
| | Amount of the Present Substance (μg/ml) | | | | | |
| Blood | 0 | 0.15 | 0.5 | 1.5 | 5 | 15 |
| Men (n = 2) | 100 | — | 99 | 108 | 101 | 119 |

(2) Experiment of addition to the blood which was allowed to stand at room temperature for 10 minutes after collection of the blood:

(Measuring method)

Measured in the same manner as in the experiment (1) The results are shown in Table 10 below.

TABLE 10

| | Coagulation Time-prolonging Ratio (%) | | | | | |
|---|---|---|---|---|---|---|
| | Amount of the Present Substance (μg/ml) | | | | | |
| Blood | 0 | 0.15 | 0.5 | 1.5 | 5 | 15 |
| Rabbit (n = 1) | 100 | 120.0 | 130.8 | 238.5 | 369.2 | 446.2 |
| Men (n = 3) | 100 | — | 115 | 133 | 141 | 160 |

As will be seen from the results of (1) and (2), the anticoagulating activity of the present substance is better when added in such a state that the coagulating system starts to function than immediately after the collection of the blood.

(3) Experiment of addition to a tissue thromboplastin-added (TTP) blood:

(i) Relationship between the concentration of added TTP and the coagulating time:

(Measuring method)

TTP was added to the rabbit blood immediately after its collectin in amounts of 0 to 4.0 μg/ml (final concentration), followed by measurement of the coagulation time in the same manner as in experiment (1). The results are shown in FIG. 1.

The results of FIG. 1 reveal that when TTP was added about 1 μg/ml, the coagulation time can be shortened to a half, thus causing the coagulation to be promoted.

(ii) Experiment of addition to TTP-added blood:

(Measuring method)

To 480 microliters of the blood obtained immediately after its collection were added 10 microliters of an aqueous physiological saline solution of TTP (final concentration 0-2 μg/ml) and 10 microliters of an aqueous physiological saline solution of the present substance (final concentration 15 μg/ml) and mixed. The coagulation time was measured in the same manner as in experiment (1).

Figure 2:
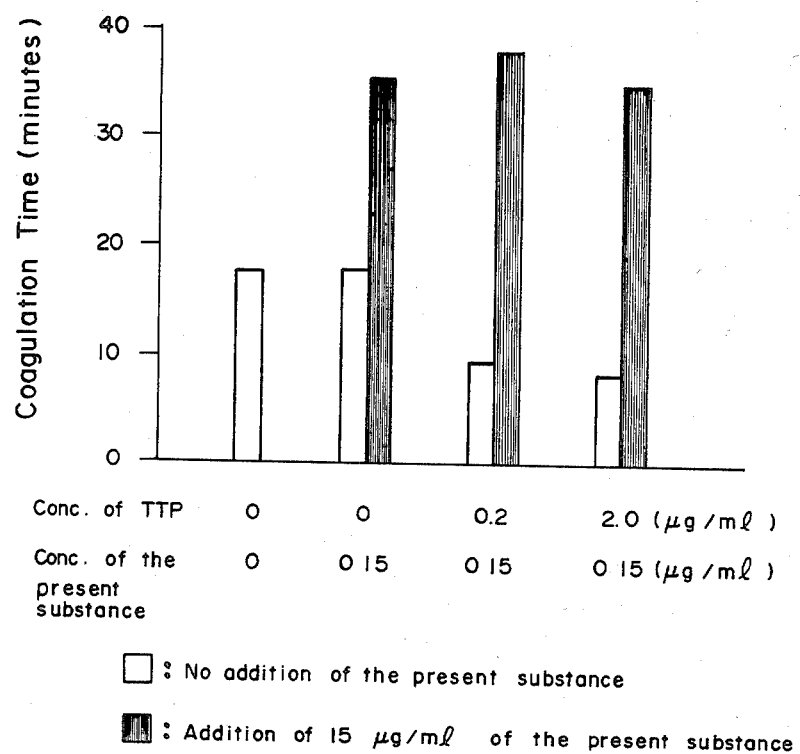
FIG. 2 is a graphical representation of the relation between concentration of TTP added to the fresh blood of rabbit and coagulation time-prolonging ratio and also of the relation between concentration of the present substance and coagulation time.
Figure 3:
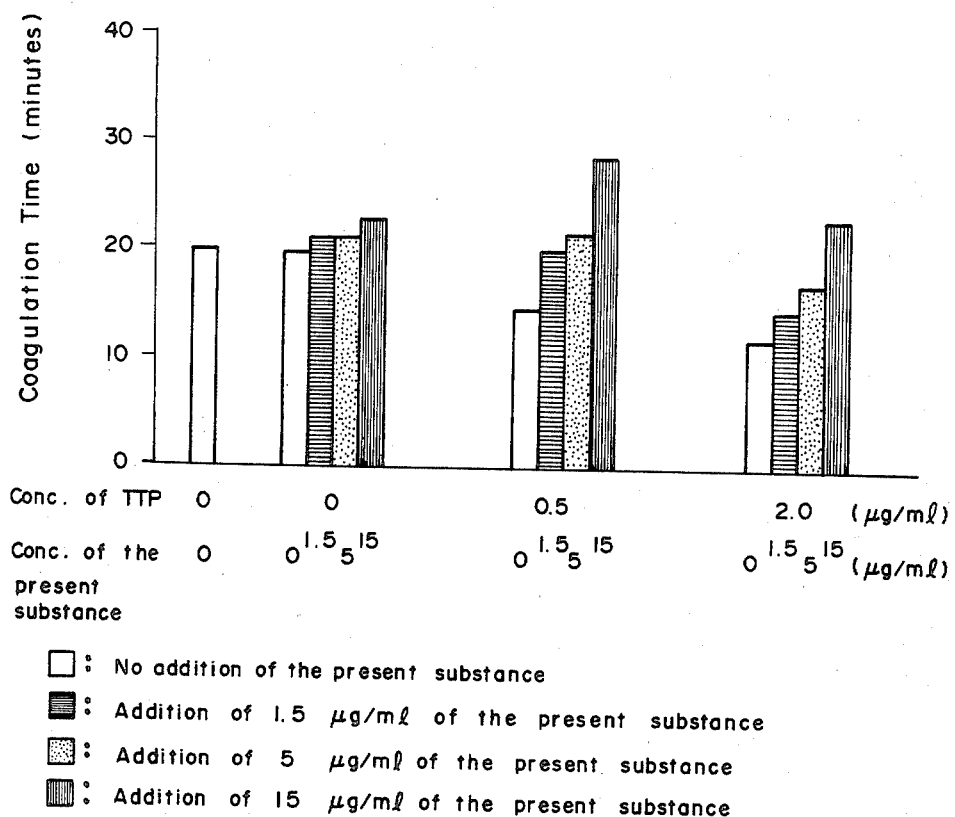
FIG. 3 is a graphical representation of the relation between concentration of TTP added to the human fresh blood and coagulation time and of the relation between concentration of the present substance added to the TTP-added blood and coagulation time.

The results using the blood of rabbit are shown in FIG. 2 and those results using the human blood are shown in FIG. 3.

From the above results, it will be seen that the anticoagulating action of the present substance develops more effective in a coagulation-exasperated state.

EXAMPLE 9

| (Preparation) | |
|---|---|
| Present substance (obtained in Example 1) | 1 mg |
| Alubmin | 5 mg |
| Mannitol | 25 mg |
| Sodium chloride | 1.95 mg |
| Sodium phosphate | 3.85 mg |

The above ingredients were dissolved in 2 ml distilled water for injection and placed in a sterile vial, followed by preliminary freezing at −30° C. to −40° C. for 2 hours, primary drying at a temperature of −30° C. to +20° C. under a vacuum of 0.05 to 0.1 Torr. for 35 hours and then secondary drying at 30° C. under a vacuum of 0.01 to 0.05 Torrs. for 5 hour, to obtain a vial for injection.

What is claimed is:

1. A human placenta-derived anticoagulating substance substantially free from glucose having the following properties:
   (1) a molecular weight, as determined by SDSpolyacrylamide gel electrophoresis, reduced state, of 34,000±2,000;
   (2) an isoelectric point, as determined by isoelectric column electrophoresis using an ampholite, of 4.7±0.1;
   (3) a stability such that said substance is
      (a) inactivated by heat treatment at 50° C. for 30 minutes,
      (b) stable at a pH of 4 to 10, and
      (c) stable in plasma at 37° C. for 30 minutes;
   (4) an activity such that said substance is
      (a) capable of prolonging a recalcification
      (b) capable of prolonging a prothrombin time,
      (c) capable of prolonging an activated partial thromboplastin time; and said substance has
   (5) an amino acid composition consisting essentially of in mole percent:

| Aspartic acid | 9.8 |
|---|---|
| Threonine | 7.0 |
| Serine | 6.3 |
| Glutamic acid | 13.3 |
| Proline | 2.0 |
| Glycine | 7.5 |
| Alanine | 8.0 |
| ½ Cystine | 0.3 |
| Valine | 4.6 |
| Methionine | 1.8 |
| Isoleucine | 5.3 |
| Leucine | 11.8 |
| Tyrosine | 3.6 |
| Phenylalanine | 4.2 |
| Histidine | 1.4 |
| Lysine | 7.2 |
| Arginine | 6.2. |

2. An anticoagulant composition comprising an effective amount of the human placenta-derived anticoagulating substance of claim 1.

3. The anticoagulant composition according to claim 2, which is in the form of a freeze-dried composition.

4. The anticoagulant composition according to claim 2, which further comprises one or more stabilizers selected from the group consisting of albumin, gelatin and mannitol.

5. The anticoagulant composition according to claim 2, wherein said effective amount is such that daily dosages in the range of from 10 μg to 10 mg/kg can be provided.

6. A process for producing the human placenta-derived anticoagulating substance according to claim 1, which comprises:
   (a) homogenizing human placenta,
   (b) subjecting the resulting homogenate to centrifugal separation, to form a supernatant and a sediment,
   (c) extracting an anticoagulating substance from the residue or from a microsome fraction contained in the supernatant with a surface active agent or a chelating agent or a mixture thereof, and (d) purifying and isolating the substance from the extract.

7. The process according to claim 6, which further comprises, after subjecting the resulting homogenate to centrifugal separation but prior to said extraction, subjecting the formed supernatant to ultracentrifugal separation at 50,000 to 100,000 x g to form a residue and a microsome fraction, which are separated and each washed with buffer, then combined together for said extraction step.

8. The process according to claim 6, which further comprises after said extraction, subjecting said extract to ammonium sulfate fractionation.

9. The process according to claim 8, wherein said ammonium sulfate factionation comprises:

(a) adding solid ammonium sulfate to the extract until reaching a 35% saturation concentration, then subjecting a formed supernatant to centrifugal separation, and then (b) adding solid ammonium sulfate to the supernatant until reaching a 85% saturation concentration, then obtaining the ammonium sulfate fraction as a precipitate by centrifugal separation.

10. A method of retarding the coagulation of blood in a mammal, which comprises administering to said mammal and effective amount of the human-placenta derived anticoagulating substance of claim 1.

* * * * *

UNITED STATES PATENT AND TRADEMARK OFFICE
CERTIFICATE OF CORRECTION

PATENT NO. : 4,732,891

DATED : Mar. 22, 1988

INVENTOR(S) : Masahiro Maki, et al.

It is certified that error appears in the above-identified patent and that said Letters Patent is hereby corrected as shown below:

Title page:

The listing for 'Attorney, Agent, or Firm' should read:

--Oblon, Fisher, Spivak, McClelland & Maier--

Signed and Sealed this

Twelfth Day of July, 1988

Attest:

DONALD J. QUIGG

Attesting Officer

Commissioner of Patents and Trademarks